(12) United States Patent
He et al.

(10) Patent No.: US 11,327,085 B2
(45) Date of Patent: May 10, 2022

(54) METHOD FOR RAPID AND QUANTITATIVE DETERMINATION OF SILDENAFIL IN COCKTAIL

(71) Applicant: Zhejiang University, Hangzhou (CN)

(72) Inventors: Yong He, Hangzhou (CN); Lei Lin, Hangzhou (CN); Pengcheng Nie, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 224 days.

(21) Appl. No.: 16/885,978

(22) Filed: May 28, 2020

(65) Prior Publication Data
US 2020/0408786 A1    Dec. 31, 2020

(30) Foreign Application Priority Data

Jun. 29, 2019  (CN) .......................... 201910581061.4
Dec. 18, 2019  (CN) ......................... 201911305396.X

(51) Int. Cl.
*G01N 33/94* (2006.01)
*G01N 21/65* (2006.01)

(52) U.S. Cl.
CPC ........... *G01N 33/94* (2013.01); *G01N 21/658* (2013.01)

(58) Field of Classification Search
CPC . G01N 33/94; G01N 2201/129; G01N 21/658
See application file for complete search history.

(56) References Cited

FOREIGN PATENT DOCUMENTS

CN        107505305 A    * 12/2017  ........... G01N 21/658

OTHER PUBLICATIONS

Espacenet English Translation of Description of CN107505305A. (Year: 2017).*
Zhao et al., Rapid Detection of Sildenafil Drugs in Liquid Nutraceuticals Based on Surface-Enhanced Raman Spectroscopy Technology, Jul. 3, 2017, Wiley, vol. 35, pp. 1522-1528. (Year: 2017).*

* cited by examiner

*Primary Examiner* — Jennifer Wecker
*Assistant Examiner* — Kathryn Elizabeth Limbaugh
(74) *Attorney, Agent, or Firm* — Nixon & Vanderhye P.C.

(57) ABSTRACT

A method for rapid and quantitative determination of sildenafil in cocktail includes the exemplary steps of: Step 1, assigning a Raman spectrum of sildenafil; Step 2, weighing and dissolving a sildenafil standard in methanol to obtain a 1,000 mg/L sildenafil standard solution, and mixing cocktails with the sildenafil standard solution, to prepare test solutions; Step 3, mixing 100 µL each of test solutions with 500 µL of surface enhancer OTR 202 to acquire Raman spectra; and Step 4, establishing a linear regression model, with a formula of y=4035.1 x+503.26, where y is the content of sildenafil in cocktail, in mg/L, and x is intensity of Raman characteristic peaks at 1584 $cm^{-1}$. Rapid determination of sildenafil by SERS is feasible and reliable, serving as a novel, rapid, and accurate method for quantitative determination of sildenafil in cocktail. The method meets the requirements of analysis and detection of sildenafil in other alcoholic beverages.

5 Claims, 5 Drawing Sheets

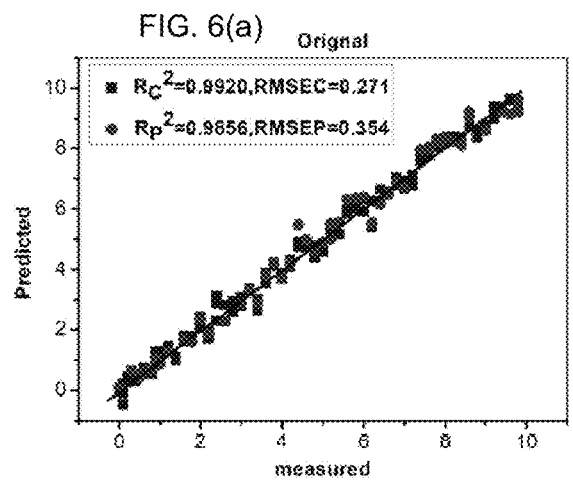
FIG. 6(a) Original
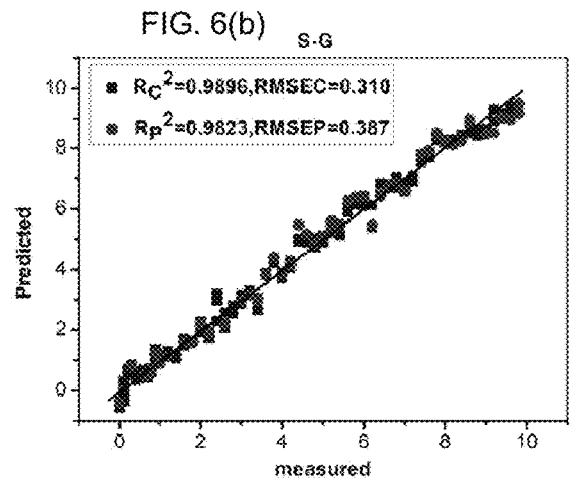
FIG. 6(b) S-G
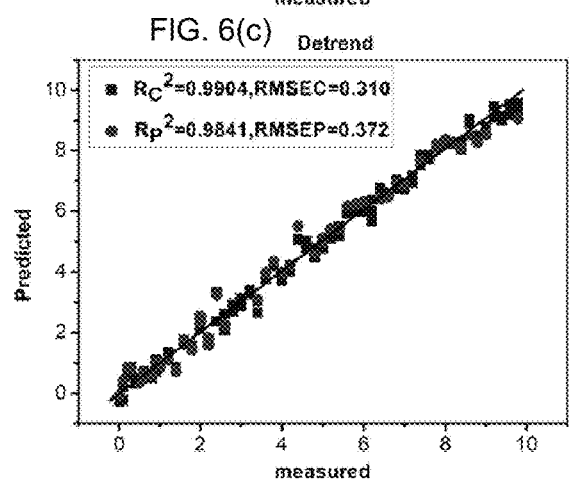
FIG. 6(c) Detrend
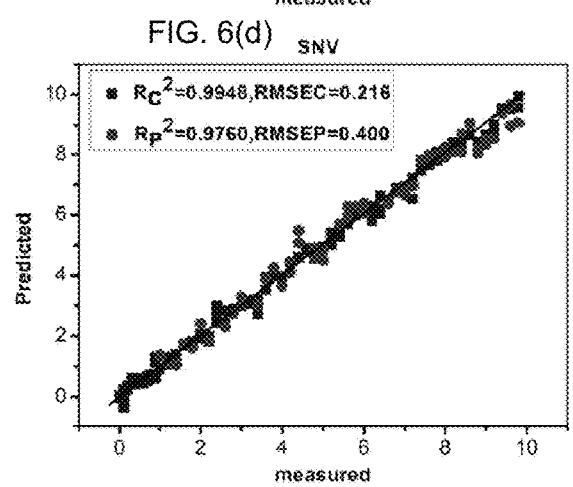
FIG. 6(d) SNV
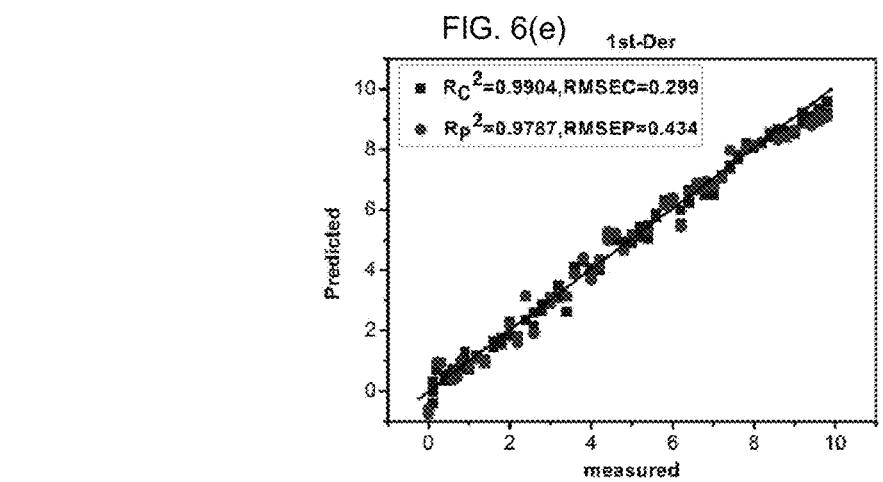
FIG. 6(e) 1st-Der

METHOD FOR RAPID AND QUANTITATIVE DETERMINATION OF SILDENAFIL IN COCKTAIL

CROSS-REFERENCES TO RELATED APPLICATIONS

This application claims the benefit of Chinese Patent Application No. 201910581061.4, filed Jun. 29, 2019, and Chinese Patent Application No. 201911305396.X, filed Dec. 18, 2019, the entire content of each of which is herein incorporated by reference.

STATEMENT REGARDING FEDERALLY SPONSORED RESEARCH OR DEVELOPMENT

NOT APPLICABLE

TECHNICAL FIELD

The present invention relates to the field of detection, and in particular to a method for rapid and quantitative determination of sildenafil in cocktail.

BACKGROUND

The following background is provided to aid the reader in understanding the described embodiments but cannot be considered as prior art.

Sildenafil (SD) and related compounds thereof are the most common adulterants found in traditional Chinese herbal preparations, which are mainly used as sexual enhancer or man's virility products. Pharmacological effect thereof is to inhibit the metabolism of the second messenger cyclic guanosine monophosphate (cGMP), promote the relaxation of cavernous artery smooth muscle, and then improve the symptoms of erectile dysfunction (ED). However, the usage of SD is controlled through medical supervision due to harmful side-effects thereof, such as headache, dyspepsia, back pain, rhinitis, flu syndrome, etc. In recent years, SD, through illegal business, has illegally added to Chinese patent medicines and alcoholic drinks in pursuit of high profits. Generally, traditional methods for determining SD in alcoholic beverages include ultraviolet (UV) spectrophotometry, high performance liquid chromatography (HPLC), gas chromatography-mass spectrometry (GC-MS), thin layer chromatography (TLC), near infrared spectroscopy (NIR), etc. Xin et al. applied HPLC method to detect seven kidney-tonifying and yang-strengthening illegal additives. It was shown that the limits of detection (LODs) were in the range of 8.2-33.4 ng.

Surface-enhanced Raman spectroscopy (SERS), which can provide ultrasensitive and unmarked chemical analysis, has attracted focus and attention in past decades. SERS is suitable for rapid screening of molecule substances' absorbed molecules because of advantages thereof of simple pretreatment, convenient equipment, and fast detection speed. However, because sildenafil content is low in cocktail, there is no research on the quantitative determination of sildenafil in cocktail by SERS.

SUMMARY

An objective of the described embodiments is to provide a novel, rapid and accurate method for the quantitative determination of sildenafil in cocktail by surface-enhanced Raman spectroscopy (SERS). The method can meet the requirements of analysis and detection of sildenafil in cocktail.

To achieve the above purpose, the described embodiments provide a method for rapid and quantitative determination of sildenafil in cocktails, including the following exemplary steps:

Step 1, assigning a Raman spectrum of sildenafil to obtain Raman characteristic peaks thereof;

Step 2, weighing and dissolving a sildenafil standard in methanol to obtain a 1,000 mg/L sildenafil standard solution, and mixing cocktails with the sildenafil standard solution, to prepare a plurality of groups of test solutions at different concentrations;

Step 3, mixing the resulting test solutions with the surface enhancer OTR 202 in a volume ratio of 1:5 to acquire Raman spectra, respectively; and Step 4, establishing a linear regression model, with a formula of y=4035.1 x+503.26, where, y is the content of sildenafil in cocktail, in mg/L, and x is intensity of the Raman characteristic peak at 1584 $cm^{-1}$, in a.u.

Preferably, in Step 1, the Raman characteristic peaks of sildenafil are in the value range of 1200-1600 $cm^{-1}$. Preferably, the Raman characteristic peaks are respectively in the value range of 1200-1250 $cm^{-1}$, 1400-1450 $cm^{-1}$, 1500-1550 $cm^{-1}$, and 1550-1600 $cm^{-1}$. Preferably, in Step 1, the Raman characteristic peaks of sildenafil are at $1235^{-1}$, $1401^{-1}$, $1530^{-1}$, 1584 $cm^{-1}$, respectively.

Preferably, in Step 2, the test solutions include 11 concentrations diluted to 0 to 1 mg/L (0.1 mg/L per gradient) and 44 concentrations diluted to 1.2 to 10 mg/L (0.2 mg/L per gradient), and there are three samples for each concentration.

Preferably, volumes of the test solution and the surface enhancer OTR 202 are 100 μL and 500 μL, respectively.

Preferably, in Steps 1 and 3, parameters of Raman spectral acquisition are set as follows: an excitation wavelength of 785 nm, a power of 100 mW, a scanning range of 200-3300 $cm^{-1}$, an optical resolution of 2 $cm^{-1}$, and an integration time of 10 s, and an average spectral value of 3 times of integration.

An advantage of the described embodiments lies in the feasibility and reliability of SERS rapid determination of sildenafil, which provides a novel, rapid and accurate method for quantitative determination of sildenafil in cocktails, and can meet the requirements of analysis and detection of sildenafil in cocktails.

BRIEF DESCRIPTION OF DRAWINGS

FIGS. 6(a)-(e) illustrate the model performance modeled by partial least squares (PLS) with different pretreatments: FIG. 6(a) Original; FIG. 6(b) Savitzky-Golay (S-G); FIG. 6(c) detrend (DT); FIG. 6(d) standard normal variation (SNV); FIG. 6(e) 1st-derivative (1st-Der).

DETAILED DESCRIPTION

Structures related in the described embodiments and technical terms used herein will be further described below. These descriptions are merely examples for explaining how to realize the described embodiments, and do not limit the invention.

A method for rapid and quantitative determination of sildenafil in cocktail was provided, including the following steps:

Step 1, Raman spectra of solid sildenafil standard and sildenafil in methanol were acquired to assign spectra thereof separately. In this step, a concentration of the sildenafil solution selected was 1,000 mg/L; parameters of Raman spectral acquisition were set as follows: an excitation wavelength of 785 nm, a power of 100 mW, a scanning range of 200-3300 $cm^{-1}$, an optical resolution of 2 $cm^{-1}$, and an integration time of 10 s, and an average spectral value of 3 times of integration. An objective of peak assignment was the qualitative identification and quantitative determination of sildenafil.

Figure 1:
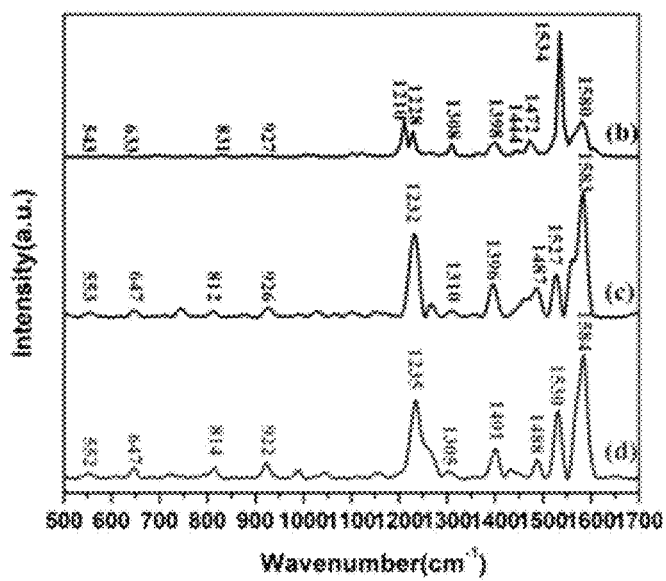
FIG. 1 is a Raman spectrum (RS) of sildenafil (SD), (b) is an RS of SD simulated by density functional theory (DFT), (c) is an RS of solid SD standard, and (d) shows SERS spectra of SD in methanol.

As shown in FIG. 1, both RS of sildenafil solid standard (c) and SERS spectrum of sildenafil in methanol (d) are basically consistent with the density functional theory (DFT) calculated Raman spectrum (b); results show that the SERS spectrum of sildenafil based on OTR 202 is feasible and reliable. The assignments of Raman characteristic peaks of sildenafil are as listed in Table 1: 552 $cm^{-1}$ is the carbonyl stretching and phenetole breathing deformable vibration, 647 $cm^{-1}$ is the carbonyl stretching, phenetole deformable vibration, and C-S stretching, and 831 $cm^{-1}$ belongs to the pyrazole pyridine stretching; 922 $cm^{-1}$ is assigned to the C-C deformable vibration and the C-H stretching in pyrazole pyridine group, 1235 $cm^{-1}$ is the C-H stretching vibration in carbonyl, 1305 $cm^{-1}$ is C-H stretching vibration, and 1401 $cm^{-1}$ is the C-H deformable vibration; 1488 $cm^{-1}$, 1530 $cm^{-1}$, and 1584 $cm^{-1}$ are the C-H deformable vibration in pyrazole pyridine.

TABLE 1

Assignments of Raman characteristic peaks of sildenafil and vibrational forms thereof

| Solid ($cm^{-1}$) | SERS ($cm^{-1}$) | Vibrational form |
|---|---|---|
| 533 (w) | 552 | $\upsilon + \delta$ |
| 647 (w) | 647 (w) | $\upsilon + \delta + \upsilon$ (C-S) |
| 812 (w) | 814 (m) | $\upsilon$ |
| 926 (w) | 922 (m) | $\delta$(C-C) + $\upsilon$(C-H) |
| 1232 | 1235 | $\upsilon$ (C-H) |
| 1310 (w) | 1305 | $\delta$(C-H) |
| 1396 (m) | 1401 (m) | $\delta$(C-H) |
| 1487 (m) | 1488 (m) | $\delta$(C-H) |
| 1527 (s) | 1530 (s) | $\upsilon$(C-H) |
| 1583 (vs) | 1584 (vs) | $\delta$(C-H) |

NOTE:
vs: very strong;
s: strong;
m: medium;
w: weak;
vw: very weak;
$\upsilon$: stretching vibration;
$\delta$: deformable vibration Step 2, a sildenafil standard was weigh and dissolve in methanol, and diluted to a 1,000 mg/L to obtain a sildenafil standard solution; cocktail was mixed with the sildenafil standard solution, to prepare a plurality of groups of test solutions at different concentrations. The test solutions included 11 concentrations diluted to 0 to 1 mg/L (0.1 mg/L per gradient) and 44 concentrations diluted to 1.2 to 10 mg/L (0.2 mg/L per gradient), and there were three samples for each concentration. Particularly, the selected cocktails were manufactured by Shanghai Bacchus Liquor Co., Ltd.

Step 3, the test solutions was mixed with the surface enhancer OTR 202 in a volume ratio of 1:5 to acquire Raman spectra, respectively.

Figure 2A:
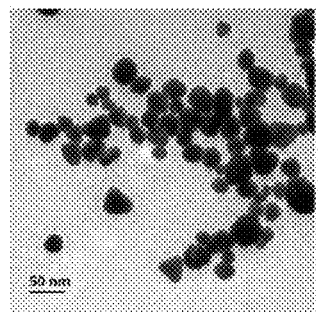
FIG. 2(a) is a transmission electron microscopy (TEM) image of OTR 202, FIG. 2(b) displays UV/Visible spectra of OTR 202.
Figure 2B:
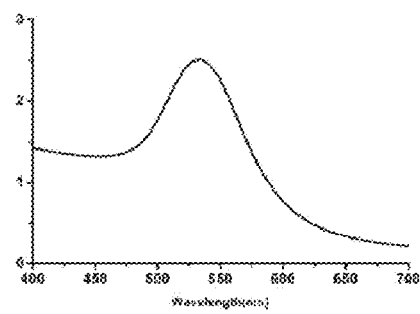
FIG. 2(c) is an SERS spectrum of OTR 202.
Figure 2C:
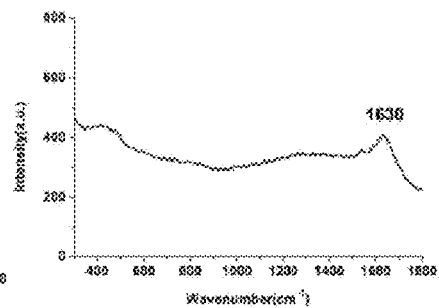

First, the structure, UV spectrum, and Raman spectroscopy (RS) of OTR 202 were analyzed. As shown in FIG. 2(a), the average diameter of OTR 202 is approximately 30 nm. As shown in FIG. 2(b), the UV/Visible characteristic absorption peaks of OTR 202 are at 533 nm. In addition, the Raman spectrum of OTR 202 only has a faint signal at 1630 $cm^{-1}$ (FIG. 2(c)), suggesting that OTR 202 per se has no strong Raman characteristic peaks and does not have an interferential effect on experimental results. Therefore, OTR 202 is suitable as SERS substrate to detect SD.

Figure 3:
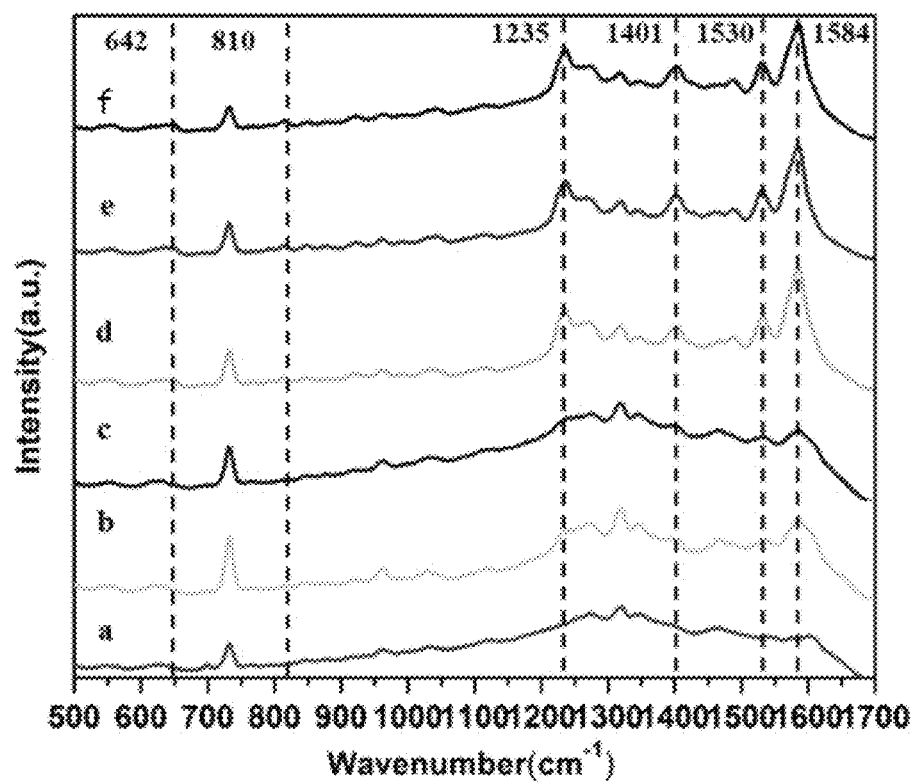
FIG. 3 is an SERS spectrum of sildenafil (SD) in cocktail, where a: 0 mg/L; b: 0.1 mg/L; c: 0.5 mg/L; d: 2 mg/L; e: 5 mg/L; f: 10 mg/L.

Subsequently, to investigate the sensitivity and stability of the OTR 202 substrates for the detection of SD in cocktail, six different SD concentrations (0, 0.1, 0.5, 2, 5, and 10 mg/L) were collected from Step 2 for Raman spectral acquisition, and the corresponding SERS were acquired. As shown in FIG. 3, the SERS intensity decreases gradually with the decrease of SD concentration from 10 mg/L to 0 mg/L. the characteristic peaks thereof are identified at 1235, 1401, 1530, and 1584 $cm^{-1}$. SD in cocktail can still be identified even when the SD solution concentration is as low as 0.1 mg/L. The limit of detection (LOD) of SD in cocktail reaches 0.1 mg/L. Therefore, 1235, 1401, 1530, and 1584 $cm^{-1}$ can be qualitatively determined as SD characteristic peaks.

Figure 4:
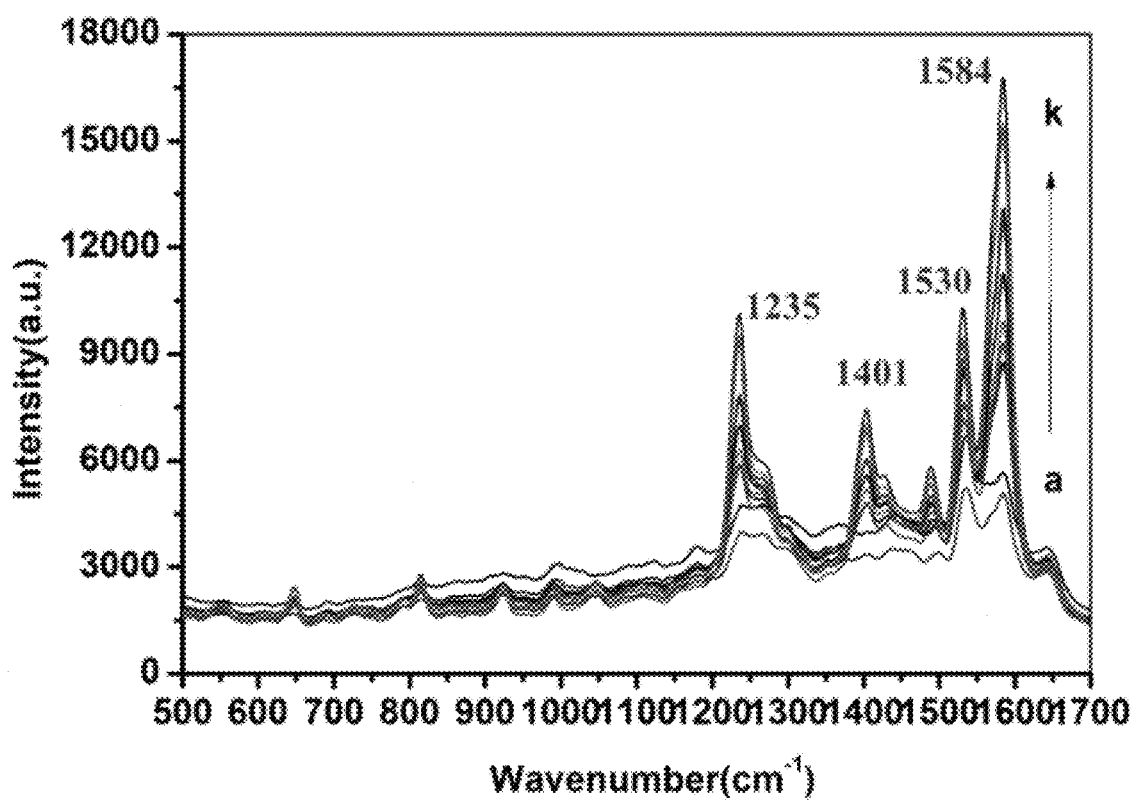
FIG. 4 shows SERS spectra of sildenafil (SD) in cocktail with different concentrations from a to k: 0.1, 0.2, 0.4, 0.6, 0.8, 1, 2, 4, 6, 8, 10 mg/L, respectively.
Figure 5A:
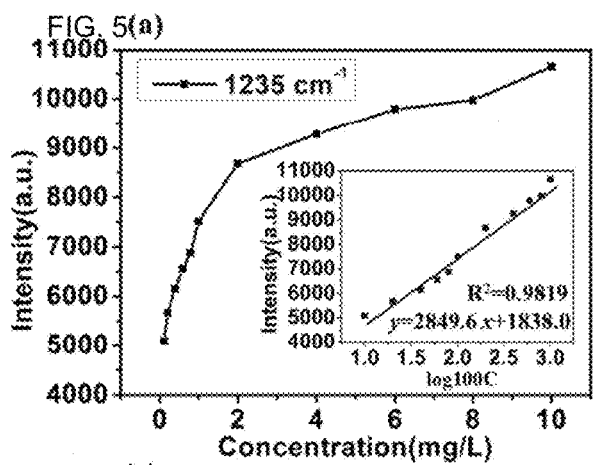
FIGS. 5(a)-(d) illustrate plots of intensities of SERS peaks of sildenafil (SD) in cocktail at 1235 $cm^{-1}$ FIG. 5(a), 1401 $cm^{-1}$ FIG. 5(b), 1530 $cm^{-1}$ FIG. 5(c), and 1584 $cm^{-1}$ FIG. 5(d) versus concentrations of SD in cocktail.
Figure 5B:
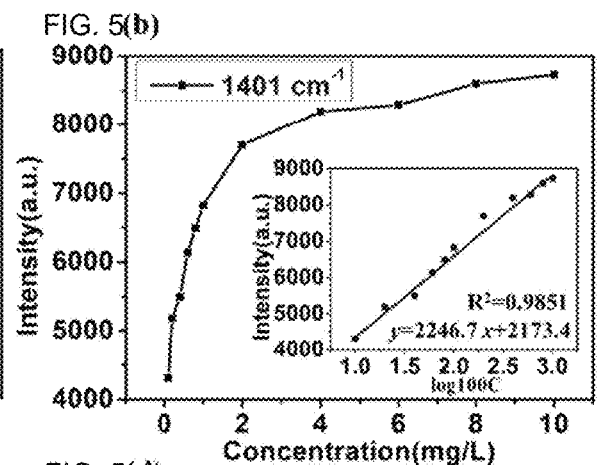
Figure 5C:
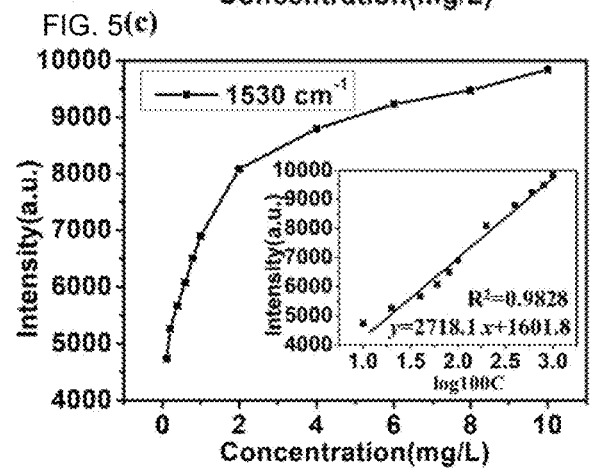
Figure 5D:
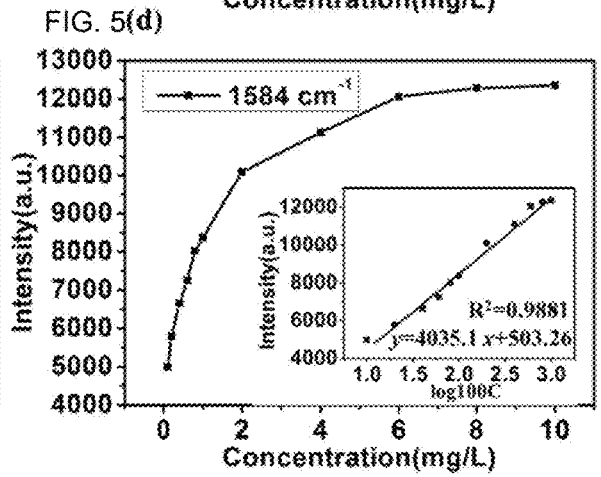

Next, to investigate the accuracy and stability of the OTR 202 substrate for the detection of SD in cocktail, 11 different concentrations of SD in cocktail (0.1, 0.2, 0.4, 0.6, 0.8, 1, 2, 4, 6, 8, 10 mg/L) were selected for Raman spectral acquisition, and acquire the corresponding SERS. As shown in FIG. 4, with the decrease of SD in cocktail from 10 mg/L to 0.1 mg/L, the Raman peaks at 1235, 1401, 1530, and 1584 $cm^{-1}$ decrease gradually. Therefore, 1235, 1401, 1530, and 1584 $cm^{-1}$ can be quantitatively determined as SD characteristic peaks in cocktail.

Step 4, linear regression equations of Raman characteristic peaks at 1235, 1401, 1530, and 1584 $cm^{-1}$ were established. In this example, the characteristic peak at 1584 $cm^{-1}$ with the maximum correlation coefficient (0.9881) was selected to establish a linear regression model, with a formula of y=4035.1x+503.26, where y was the content of sildenafil in cocktail, in mg/L, and x was intensity of the Raman characteristic peak at 1584 $cm^{-1}$, in a.u.

FIGS. 5(a)-(d) illustrate the establishment of linear regression equations of the Raman characteristic peaks at 1235, 1401, 1530, and 1584 $cm^{-1}$. As shown in FIGS. 5(a)-(d), SERS spectra of SD in cocktail mixed with the OTR 202 are concentration dependent. The peaks at 1235, 1401, 1530, and 1584 $cm^{-1}$ could be regarded as a marker band for SD in cocktail determination owing to drastic intensity change thereof with varying SD concentration. There was a good linear correlation between Raman peak intensity and logarithm of SD concentration in cocktail in each linear regression equation ranged from 0.1 mg/L to 10 mg/L ($0.9822 < R^2 < 0.9860$), demonstrating that the SERS can accurately and quantitatively analyze SD in cocktail.

To verify the accuracy of this method, four linear models in FIGS. 5(a)-(d) were used to predict samples with eight different concentrations of SD in cocktail, where four linear models included: y=2849.6x+1838.0, where x was the intensity of Raman characteristic peaks at 1235 cm$^{-1}$; y=2246.7x+2173.4, where x was the intensity of Raman characteristic peaks at 1401 cm$^{-1}$; y=2718.1x+1601.8, where x was the intensity of Raman characteristic peaks at 1530 cm$^{-1}$; y=4035.1x+503.26, where x was the intensity of Raman characteristic peaks at 1584 cm$^{-1}$.

and a wavelength to a trend line according to a polynomial, and then subtracts the trend line from the original spectrum to achieve the trend effect, which belongs to the prior art. 1st-Der can distinguish overlapping peaks, eliminate the interference from other backgrounds, and improve the resolution, sensitivity and signal-to-noise ratio of the spectrum. Both calibration set and prediction set of samples are divided by SPXY method, and the proportion of calibration set and prediction set is about 2:1; PLS model is established. The PLS modeling results based on 500-1700 cm$^{-1}$ spectra under different pretreatments are shown in Table 3.

TABLE 2

Measured and predicted values of sildenafil in cocktail

| Measured value (mg/L) | Peak (cm$^{-1}$) | Predicted value (mg/L) | RSD (%) | Recovery (%) | Measured value (mg/L) | Peak (cm$^{-1}$) | Predicted value (mg/L) | RSD (%) | Recovery (%) |
|---|---|---|---|---|---|---|---|---|---|
| 0.3 | 1235 | 0.326 | 2.87 | 108.87 | 0.5 | 1235 | 0.416 | 5.67 | 82.32 |
|  | 1401 | 0.255 | 4.83 | 85.17 |  | 1401 | 0.454 | 4.19 | 90.80 |
|  | 1530 | 0.307 | 1.25 | 100.25 |  | 1530 | 0.470 | 3.35 | 94.65 |
|  | 1584 | 0.242 | 5.3 | 80.69 |  | 1584 | 0.468 | 3.37 | 93.62 |
| 0.7 | 1235 | 0.589 | 5.82 | 84.17 | 0.9 | 1235 | 0.101 | 9.20 | 111.19 |
|  | 1401 | 0.673 | 4.19 | 90.81 |  | 1401 | 0.996 | 8.66 | 110.66 |
|  | 1530 | 0.564 | 6.38 | 80.62 |  | 1530 | 0.952 | 5.81 | 105.81 |
|  | 1584 | 0.607 | 4.23 | 86.8 |  | 1584 | 0.843 | 5.62 | 89.37 |
| 3 | 1235 | 2.95 | 1.39 | 98.61 | 5 | 1235 | 4.80 | 3.93 | 96.07 |
|  | 1401 | 2.84 | 5.30 | 94.70 |  | 1401 | 5.40 | 4.17 | 108.17 |
|  | 1530 | 2.80 | 4.53 | 93.47 |  | 1530 | 4.52 | 3.56 | 90. |
|  | 1584 | 3.53 | 6.75 | 117.74 |  | 1584 | 5.01 | 1.29 | 100.30 |
| 7 | 1235 | 5.89 | 4.82 | 84.17 | 9 | 1235 | 10.1 | 4.20 | 111.19 |
|  | 1401 | 6.73 | 9.19 | 90.81 |  | 1401 | 9.96 | 5.66 | 110.66 |
|  | 1530 | 5.64 | 5.38 | 80.62 |  | 1530 | 9.52 | 2.81 | 105.81 |
|  | 1584 | 6.07 | 3.23 | 86.8 |  | 1584 | 8.43 | 3.62 | 89.37 |

According to table 2, relative standard deviations (RSDs) between measured and predicted values of SD in cocktail range from 1.25% to 6.75%, and recoveries thereof range from 80.62% to 117.74%. Results show that the predicted value of this method is basically consistent with the measured value thereof, suggesting that the rapid determination of SD by SERS is feasible and reliable.

As a further example, in Step 4, a partial least square model was used in the discriminant analysis of the spectral data.

Considering that the Raman peaks of SD in cocktail were mainly distributed in the range of 500-1700 cm$^{-1}$, the partial least squares (PLS) prediction model was established based on 500-1700 cm$^{-1}$ SERS spectra. The SERS spectra of SD in cocktail of 155 samples were obtained and then pretreated with Savitzky-Golay (S-G), detrend (DT), standard normal variation (SNV), and 1st-derivative (1st-Der), respectively, and then modeled by PLS. SERS spectra are easily affected by the fluorescence background. Therefore, removing the background fluorescence from the Raman signal it is very important for accurate analysis of the Raman signals. Thus, in the PLS model, each original SERS spectrum was processed by S-G 5-point smoothing filter, DT, SNV and 1st-DER to remove the fluorescence background from Raman signals, respectively. The principle of SNV algorithm is that absorbance value at each wavelength point satisfies certain distribution in each spectrum, and spectral correction is carried out according to this assumption, which is the prior art. DT algorithm first fits a spectral absorbance

TABLE 3

The PLS modeling results of SD in cocktail based on 500-1700 cm$^{-1}$ spectra under different pretreatments

| Pretreatment | Principal Components | Calibration | | Prediction | |
|---|---|---|---|---|---|
|  |  | Rc$^2$ | RMSEC | Rp$^2$ | RMSEP |
| Original | 9 | 0.9920 | 0.271 | 0.9856 | 0.354 |
| S-G | 8 | 0.9896 | 0.310 | 0.9823 | 0.387 |
| DT | 8 | 0.9904 | 0.310 | 0.9841 | 0.372 |
| SNV | 10 | 0.9948 | 0.216 | 0.9760 | 0.400 |
| 1st-Der | 8 | 0.9904 | 0.299 | 0.9787 | 0.434 |

From effects of the prediction model in Table 3 and FIGS. 6(a)-(e), the predictive effect of SD in cocktail was great ($0.9896 < Rc^2 < 0.9948$, $0.216 < RMSEC < 0.310$; $0.9760 < Rp^2 < 0.9856$, $0.354 < RMSEP < 0.434$). Moreover, the modeling effect was similar after using different pretreatment methods. Among them, the SERS original spectra performed a slightly better modeling effect compared with SNV and 1st-Der, indicating that the background noise had little effect on the original spectrum, and the PLS model with good effect could be established through the original spectrum.

The embodiments shown and described herein may be practiced in the absence of any elements or limitations, specifically disclosed herein. The terms and expressions that have been employed herein are used as terms of description and not of limitation, and there is no intention in the use of such terms and expressions to exclude equivalents of the features shown and described or portions thereof, it being recognized that various modifications should be feasible within the scope of the described embodiments. Therefore, it should be understood that the described embodiments are disclosed by various examples and optional features, but variations and modifications of concepts described herein can be used by those of ordinary skill in the art, and those variations and modifications are believed to fall within the scope of the described embodiments limited by the appended claims.

The contents of the articles, patents, patent applications, and all other literature and available electronically information described or depicted herein are incorporated herein by reference as if each individual publication is specifically and individually indicated for reference. Applicants reserve the right to incorporate any and all materials and information from any such articles, patents, patent applications or other literature into this application.

The invention claimed is:

1. A method for rapid and quantitative determination of sildenafil in cocktails, comprising the following steps:
   Step 1, assigning a Raman spectrum of sildenafil to obtain Raman characteristic peaks thereof;
   Step 2, weighing and dissolving a sildenafil standard in methanol to obtain a 1,000 mg/L sildenafil standard solution, and mixing cocktails with the sildenafil standard solution, to prepare a plurality of groups of test solutions at different concentrations;
   Step 3, mixing the resulting test solutions with the surface enhancer OTR 202 in a volume ratio of 1:5 to acquire Raman spectra, respectively; and
   Step 4, establishing a linear regression model, with a formula of y=4035.1 x+503.26, wherein, y is the content of sildenafil in cocktail, in mg/L, and x is intensity of the Raman characteristic peak at 1584 $cm^{-1}$, in a.u.

2. The method for rapid and quantitative determination of sildenafil in cocktail according to claim 1, wherein in Step 1, the Raman characteristic peaks of sildenafil are at 1235, 1401, 1530, 1584 $cm^{-1}$, respectively.

3. The method for rapid and quantitative determination of sildenafil in cocktail according to claim 1, wherein in Step 2, the test solutions comprise 11 concentrations diluted to 0 to 1 mg/L (0.1 mg/L per gradient) and 44 concentrations diluted to 1.2 to 10 mg/L (0.2 mg/L per gradient), and there are three samples for each concentration.

4. The method for rapid and quantitative determination of sildenafil in cocktail according to claim 1, wherein volumes of the test solution and the surface enhancer OTR 202 are 100 μL and 500 μL, respectively.

5. The method for rapid and quantitative determination of sildenafil in cocktail according to claim 1, wherein in Steps 1 and 3, parameters of Raman spectral acquisition are set as follows: an excitation wavelength of 785 nm, a power of 100 mW, a scanning range of 200-3300 $cm^{-1}$, an optical resolution of 2 $cm^{-1}$, and an integration time of 10 s, and an average spectral value of 3 times of integration.

* * * * *